(12) United States Patent
Spiro et al.

(10) Patent No.: US 6,303,585 B1
(45) Date of Patent: Oct. 16, 2001

(54) CROSS-LINKED POLYSACCHARIDE DRUG CARRIER

(75) Inventors: Robert C. Spiro, Half Moon Bay; Andrea Y. Thompson, Mountain View; LinShu Liu, Sunnyvale, all of CA (US)

(73) Assignee: Orquest, Inc., Mountain View, CA (US)

( * ) Notice: Subject to any disclaimer, the term of this patent is extended or adjusted under 35 U.S.C. 154(b) by 0 days.

(21) Appl. No.: 09/110,381

(22) Filed: Jul. 1, 1998

Related U.S. Application Data

(63) Continuation-in-part of application No. 08/887,994, filed on Jul. 3, 1997, now abandoned.

(51) Int. Cl.$^7$ .......................... C08B 37/00; A61K 31/715
(52) U.S. Cl. ..................... 514/54; 514/2; 514/44; 514/54; 514/56; 514/59; 536/3; 536/21; 536/53; 536/112; 536/123.1
(58) Field of Search .................... 536/3, 21, 53, 536/112, 123.1; 514/54, 56, 59, 2.44

(56) References Cited

U.S. PATENT DOCUMENTS

| | | | |
|---|---|---|---|
| 4,931,546 | 6/1990 | Tardy et al. | 530/356 |
| 5,128,326 | 7/1992 | Balazs et al. | 514/54 |
| 5,645,587 * | 7/1997 | Chanda et al. | 623/11 |
| 5,677,276 * | 10/1997 | Dickerson et al. | 514/8 |
| 5,904,717 * | 5/1999 | Brekke et al. | 623/16 |

FOREIGN PATENT DOCUMENTS

| | | |
|---|---|---|
| 96/41813 * | 12/1996 | (WO) . |
| 97/22371 * | 6/1997 | (WO) . |

OTHER PUBLICATIONS

Fransson *Biochimica et Biophysioca Acta* 1976, 106–115.*
Streitwieser et al. Introduction to Organic Chemistry, Macmillan Publishing Company, Inc., New York, 1976, pp. 378–381.*

* cited by examiner

Primary Examiner—Kathleen Kahler Fonda
(74) Attorney, Agent, or Firm—Fish & Richardson P.C.

(57) ABSTRACT

A carrier and a method for preparing it are provided for use in the delivery of therapeutic agents. A polysaccharide is reacted with an oxidizing agent to open sugar rings on the polysaccharide to form aldehyde groups. The aldehyde groups are reacted to form covalent oxime linkages with a second polysaccharide and each of the first and second polysaccharide is selected from the group consisting of hyaluronic acid, dextran, dextran sulfate, chondroitin sulfate, dermatan sulfate, keratan sulfate, heparan, heparan sulfate and alginate.

30 Claims, 1 Drawing Sheet

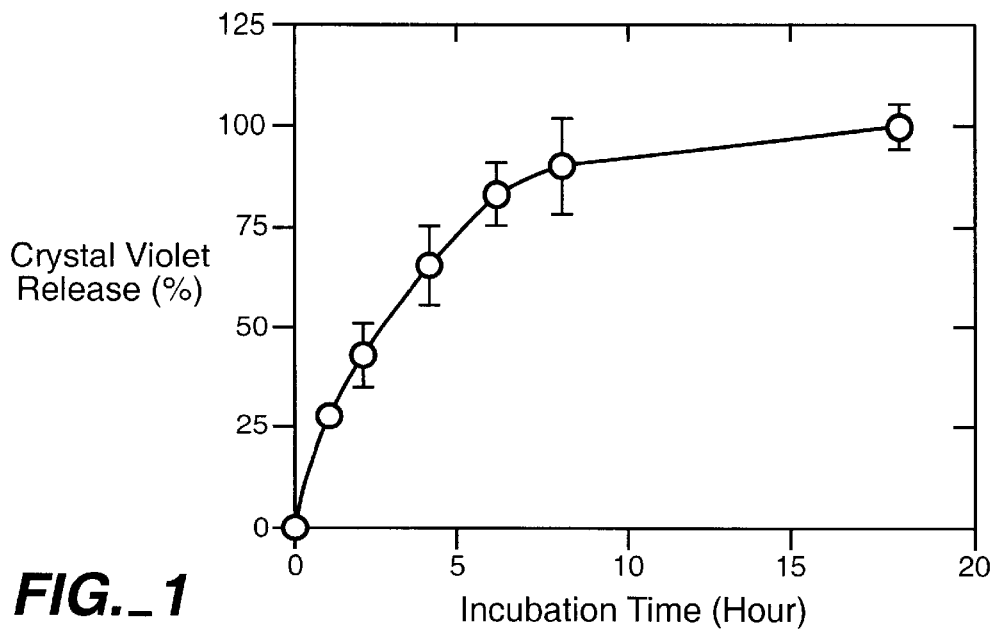
FIG._1
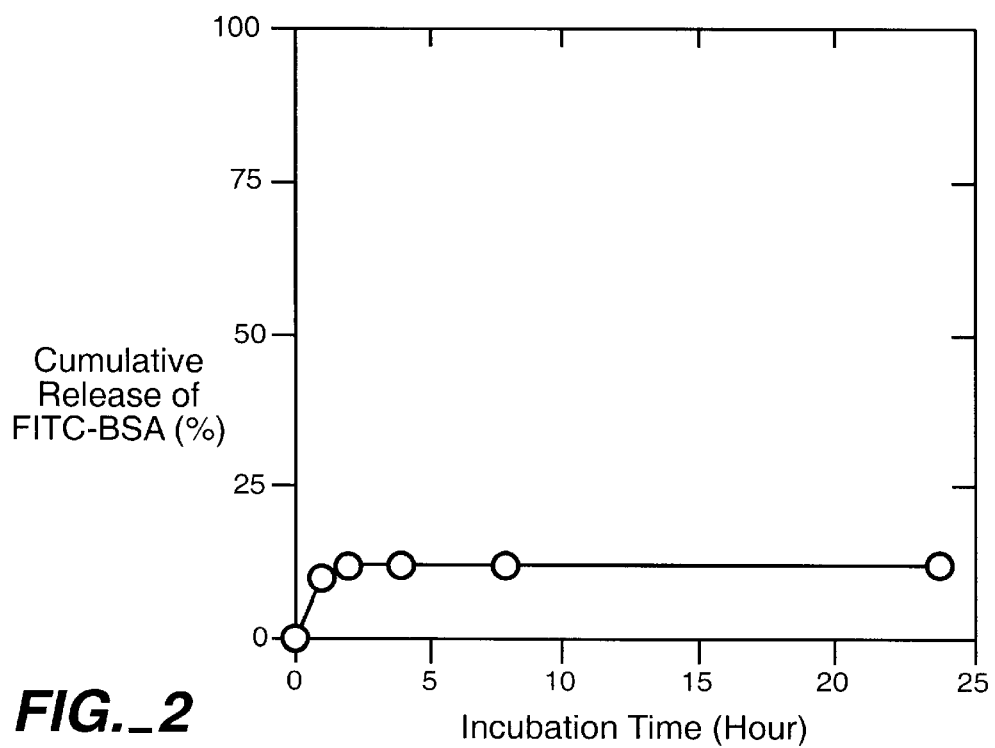
FIG._2

CROSS-LINKED POLYSACCHARIDE DRUG CARRIER

CROSS REFERENCE TO RELATED APPLICATIONS

This application is a continuation-in-part of U.S. application Ser. No. 08/887,994, filed Jul. 3, 1997, now abandoned.

BACKGROUND OF THE INVENTION

The present invention is directed to biodegradable carriers for the delivery of therapeutic agents, methods of making the carriers and methods of using the carriers.

There is a clinical demand for carriers of therapeutic agents that are biodegradable, biocompatible and which allow for targeted delivery and controlled release of the therapeutic agent.

Polysaccharides, such as hyaluronic acid (HA) and dextran sulfate have been used in a wide variety of biomaterials. Hyaluronic acid (HA), a naturally-occurring polysaccharide, has been used in matrix engineering in ophthalmic and orthopedic medicine. Clinical indications for HA alone are limited by its physical properties and the short residence time of the natural HA molecule. A formaldehyde cross-linked HA, Hylan, has been used in viscosupplementation of arthritic diseased joints (Takigami et al., 1993, Carbohydrate Polymers 22: 153–160). Dextran sulfate, a glycosaminoglycan-like polyionic derivative of dextran, has been shown to be useful as a biomaterial and drug for treatment of hyperlipidemia. It is produced by esterification of dextran, a hydrophilic polymer of glucose synthesized by certain strains of bacteria.

Berg et al., (U.S. Pat. No. 5510418, issued Apr. 4, 1996) disclose glycosaminoglycans, such as, HA, chondroitin sulfates, keratan sulfates, chitin and heparin, chemically conjugated to a synthetic hydrophilic polymer, such as polyethylene glycol (PEG) that are used as injectable formulations or solid implants. Koji Kimata et al., (U.S. Pat. No. 5464942 issued Nov. 7, 1995) disclose phospholipid linked glycosaminoglycans and their use as metastasis inhibitors. Sakurai, et al, U.S. Pat. No. 5,310,881 issued May 10, 1994, disclose glycosaminoglycan-modified proteins. Balazs et al., U.S. Pat. No. 5,128,326 issued Jul. 7, 1992, disclose hyaluronan cross-linked with divinyl sulfone.

SUMMARY OF THE INVENTION

The present invention provides biodegradable carriers for the delivery of therapeutic agents, methods of making the carriers and methods of using the carriers.

A biodegradable carrier of the present invention comprises a cross-linked first and second polysaccharide, wherein each of the first and the second polysaccharide is a derivative of a member selected from the group consisting of hyaluronic acid, dextran, dextran sulfate, chondroitin sulfate, dermatan sulfate, keratan sulfate, heparin, heparan sulfate and alginate. The first polysaccharide contains aldehyde groups derived from oxidized sugar rings. The second polysaccharide an amine derivative and the first and second polysaccharides are covalently cross-linked through these groups which forms imine linkages. In the present invention, the cross-linking reaction proceeds without utilizing extraneous cross-linking or ionic binding agents.

The method of making the biodegradable carriers comprises the steps of oxidizing a first polysaccharide to form a first polysaccharide derivative having aldehyde groups, and reacting the first polysaccharide derivative with a second polysaccharide amine derivative under conditions such that the aldehyde groups covalently react with the amine sites to form a cross linked carrier.

The present invention also provides methods of using the carrier to deliver therapeutic agents by administering the carrier at the sites of desired therapeutic intervention.

The ratios of the first and second polysaccharide can be varied to change both the physical and biological properties of the carrier. For example, a higher ratio of aldehyde bearing polysaccharide would be preferred for immobilizing a therapeutic agent to the carrier. The presence of unreacted but active aldehydes provides sites for covalent linkage to a therapeutic agent.

A carrier of the present invention can be produced in a variety of physical forms. For example, it can be made into a gel-like form for injection or a sponge-like form for implantation at a desired site of therapeutic intervention.

A carrier of the present invention provides the advantage of being biocompatible while maintaining a prolonged biodegradation rate due to the cross-linking; providing controlled release of the therapeutic agent and having the flexibility of formulation in gel-like or sponge-like form to accommodate desired therapeutic intervention.

As used herein therapeutic agent means any bioactive agent, such as a protein, polypeptide, or amino acid, including growth factors, growth factor receptors, cytokines, hormones, antibodies or chemical agents, such as, for example, non-peptide hormones chemical mimetics of growth factors and receptors that have been shown to have a biological effect.

BRIEF DESCRIPTION OF THE DRAWINGS

FIG. 1 illustrates the release of crystal violet encapsulating within a carrier of the present invention.

FIG. 2 illustrates the release of FITC-BSA immobilized within a carrier of the present invention.

DESCRIPTION OF THE PREFERRED EMBODIMENTS

The method of preparing a carrier of the present invention comprises the steps of opening sugar rings on a first polysaccharide and oxidizing terminal hydroxy groups to aldehydes using, for example, sodium or potassium periodate as a selective oxidizing agent. The amount of aldehyde groups produced in this manner can be stoichiometrically controlled. Typically, from about 1% to 50% of the rings can be opened in this manner. More preferably about 1% to 10% of the repeat sugar units are opened to form aldehyde groups. These aldehyde groups can form covalent imine crosslinks with the second polysaccharide amine derivative at amine sites. The reagents for opening sugar rings on the first polysaccharide may be any selective oxidizing agent which oxidizes a terminal hydroxyl group to an aldehyde, including specific sugar oxidases.

In the present invention the first and second polysaccharides are each selected from the group consisting of hyaluronic acid, dextran, dextran sulfate, chondroitin sulfate, dermatan sulfate, keratan sulfate, heparin, heparan sulfate and alginate. In a preferred embodiment, the first and second polysaccharides are each selected from the group consisting of hyaluronic acid and chondroitin sulfate. As used herein, the term polysaccharide includes the polysaccharide and its salts such as the sodium, potassium, magnesium, calcium, and the like, salts. Preferred forms of starting material of the polysaccharides include those which have been approved for human use. The starting material for hyaluronate can be derived by bacterial fermentation or through isolation from rooster combs or can be obtained from commercial sources.

The carrier may be comprised of the same or different first and second polysaccharides. In one preferred embodiment, the first and second polysaccharide are both hyaluronic acid. In another preferred embodiment, one polysaccharide is HA and the other is chondroitin sulfate. Typically, the polysaccharides will have an average molecular weight of about 1,000 to 10,000,000 DA.

A carrier of the present invention may be formulated in several physical forms, including gel-like or sponge-like forms. When it is desirable to obtain sustained or slow release delivery of the therapeutic agent, the agents may be immobilized by attachment to the carrier. A carrier gel, sponge, or microparticle preparation can be prepared by using a polysaccharide polyaldehyde derivative in excess, resulting in a carrier having unreacted, while still active aldehydes which are suitable for the immobilization of free amine containing bioactive therapeutic agents. Proteins and many growth factors are free amine-containing compounds.

Where it is desirable to achieve short term delivery of a therapeutic agent, the agent may be entrapped within the carrier. Drugs, growth factors, polypeptides, proteins, and other bioactive therapeutic agents can be entrapped within the gel/sponge either by mixing the agent with one of the two derivatives before gelatinization, or diffusion from a drug solution into the gel/sponge after their formation.

The agent may also be covalently linked to the carrier, for example, via an imine bond. Some of the aldehyde groups on the carrier, prior to forming a gel or sponge, may be reacted with amine groups on the agent.

The carrier may be formulated into a gel-like carrier when it is desirable to produce an injectable formulation, which can be delivered arthroscopically, or by syringe or catheter. Alternatively, the carrier may be formulated into a sponge-like carrier when it is desirable to produce an implantable formulation. The carriers of the present invention may be formed into any shape by lyophilization or air drying in molds of the desired shape. The lyophilized material may also be formed into a viscous gel by rehydrating the lyophilized material.

Examples of therapeutic agents which may be used in the present invention are not particularly restricted and include proteins originating from various animals including humans, microorganisms and plants as well as those produced by chemical synthesis and using genetic engineering techniques. Therapeutic agents include, but are not limited to, growth factors such as, bFGF, aFGF, EGF (epidermal growth factor), PDGF (platelet-derived growth factor), IGF (insulin-like growth factor), TGF-β 1 through 3, including the TGF-β superfamily (BMP's, GDF-5, ADMP-1 and dpp); cytokines, such as various interferons, including interferon-alpha, -beta and -gamma, and interleukin-2 and -3; hormones, such as, insulin, growth hormone-releasing factor and calcitonin; non-peptide hormones; antibiotics; anti-cancer agents and chemical agents, such as, chemical mimetics of growth factors or growth factor receptors, and DNA constructs, including cDNA constructs and genomic constructs). In a preferred embodiment, the therapeutic agents include those factors, proteinaceous or otherwise, which are found to play a role in the induction or conduction of growth of bone, ligaments, cartilage or other tissues associated with bone or joints, such as for example, BMP and bFGF. The present invention also encompasses the use of autologous or allogeneic cells encapsulated within the carrier. The autologous cells may be those naturally occurring in the donor or cells that have been recombinantly modified to contain nucleic acid encoding desired protein products.

As will be understood by those of skill in the art, the amount of therapeutic agent to be immobilized or encapsulated within the carrier will vary depending upon the intended therapeutic target, but will usually be in the range of picogram to gram quantities.

A carrier of the present invention may be administered through implantation, direct application or injection depending on the intended therapeutic application, the physical properties and the ratio of polysaccharide derivatives.

The efficacy of therapeutic delivery of such agents can be shown by both in vitro and in vivo tests known by those of ordinary skill in the art. In the present invention, the preferred therapeutic agents are those factors which are found to play a role in the induction or conduction of growth of bone, ligaments, soft tissue, cartilage or other tissues associated with bone or joints.

In vitro and in vivo assays for the assessment of chondroinduction, chondroconduction, osteoinduction and osteoconduction are known by those of ordinary skill in the art. For the in vitro tests, primary fetal rat calvarial cells, harvested by a series of collagenase digestions, according to the method of Wong and Cohn (*PNAS USA* 72:3167–3171, 1975), or primary rat epiphyseal cartilage Thyberg and Moskalewski, (*Cell Tissue Res.* 204:77–94, 1979) or rabbit articular chondrocytes, harvested by the method of Blein-Sella O. et al., (*Methods Mol. Biol.,* 43:169–175, 1995), are seeded into the carriers containing desired agents and cultured under conventional conditions for 1–4 weeks. Cultures are then processed and evaluated histologically.

The chondroconductive or chondroinductive capability of a carrier of the present invention containing a desired therapeutic agent can be determined by successful support of adhesion, migration, proliferation and differentiation of primary rat bone marrow and stromal cells as well as primary rat or rabbit chondrocytes. Bone marrow and bone marrow stromal cells are the source of chondroprogenitor cells found in the subchondral bone marrow of full-thickness defects. Bone marrow can be harvested from the long bones of 2–3 week-old inbred Lewis rats and can be added directly to a carrier or cultured for 2 weeks under standard conditions. The adherent stromal cell population that grows out of these cultures are passaged and frozen for use. Cells from up to six passages are used for culturing or seeding on the carrier to test for chondroconductive or chondroinductive capabilities.

Retinoic acid-treated chondrocytes represent a less mature chondrocyte and can be used to test the ability of matrices to support later stages of chondrogenesis. Retinoic acid treatment of primary chondrocytes is performed prior to culturing or seeding the cells on a carrier (Dietz, U. et al., 1993, *J. Cell Biol.* 52(1):57–68).

Cell adhesion and proliferation are monitored using an MTS assay that can measure cell number and viability based on mitochondrial activity. Stromal cells or chondrocytes are cultured on a carrier containing a therapeutic agent for 6–18 hrs. in the presence or absence of serum for adhesion analysis and for 1–2 weeks for proliferation assessment.

For cell migration testing, carriers containing therapeutic agents are coated or fitted onto porous Trans-well membrane culture inserts (Corning). Stromal cells are seeded on top of the carrier in the upper chamber of the Trans-well and a chemoattractant (growth factor, PDGF) to placed in the bottom chamber. After 12–18 hrs of culture the cells that have migrated through the carrier to the bottom side of the Trans-well membrane are quantitated by the MTS assay. The carrier is removed from the upper chamber and processed histologically to assess the degree of infiltration.

The analysis of differentiation markers relevant to chondrogenesis and osteogenesis are evaluated at both the protein and transcriptional level. The specific markers that may be analyzed include: 1) Type II collagen and IIA, IIB isoforms; 2) Aggrecan proteoglycan; 3) Type IX, X and XI collagen; 4) Type I collagen; 5) Cartilage matrix protein (CMP); 6) Cart-1 transcription factor; 7) Fibronectin (EDA, EDB isoforms); 8) Decorin proteoglycan; 9) Link protein; 10) NG-2 proteoglycan; 11) Biglycan proteoglycan; 12) Alkaline phosphatase. Differentiation may be measured by Northern/PCR analysis, Western blotting or by metabolic cell labeling.

For Northern/PCR analysis, RNA is isolated by standard procedures from stromal cells or chondrocytes. Time course tests may be used to determine optimal culture periods that range from 1 to 6 weeks depending on the cell type. The isolated RNA is analyzed by Northern gel and hybridization techniques with specific cDNA or PCR amplified probes. Northern analysis is quantified by densitometric scanning of autoradiographs and normalization to housekeeping gene signals (G3PDH). Northern analysis may be supplemented with quantitative PCR analysis using primers generated from the published cDNA sequences of the genes to be analyzed.

For Western blotting, solubilized protein lysates are isolated from cells cultured on carriers containing osteogenic or chondrogenic agents by standard techniques (Spiro R. C., et al., 1991, *J. Cell. Biol.*, 115:1463–1473). After the lysis of cells the carrier is extracted in stronger denaturants (8 M urea, GnHCL) to remove and examine bound or incorporated proteins. Protein samples are analyzed by standard Western blotting techniques using specific polyclonal or monoclonal antibodies.

For metabolic cell labeling, cells cultured on a carrier containing a therapeutic agent are metabolically radiolabeled with $^{35}SO_4$, $^{35}S$-methionine or $^3H/^{14}C$-labeled amino acids by standard techniques (Spiro et al., supra). Solubilized cellular and matrix-associated proteins are quantitatively immunoprecipitated with antibodies specific for the protein of interest and analyzed by SDS-PAGE (Spiro et al., supra). Quantitation of results are performed by densitometric scanning of autoradiographs and signals will be normalized to either cell equivalents or to a house-keeping protein such as actin.

Additionally, the ability of a carrier of the present invention containing a chrondrogenic agent to support chondrogeneic differentiation in vivo may be tested in an inbred rat soft tissue implant model. Rat bone marrow or stromal cells described above are seeded onto the carrier at high density, cultured overnight in MEM medium containing 10% FBS serum and antibiotics, then transferred into Millipore diffusion chambers and implanted intraperitoneally or subcutaneously into 8 week-old recipients. Chambers are harvested after 3 weeks and evaluated histologically for cartilage formation.

A transplantation model in outbred rats is used to evaluate the ability of the carrier containing the chondrogenic agent to maintain the cartilage phenotype in vivo. Rib costal cartilage chondrocytes are seeded onto the carrier at high density and cultured overnight in Hams F-12 containing 1% rat serum and antibiotics. The seeded carriers are then implanted into posterior tibial muscle pouches created by blunt dissection in 8 week-old male Sprague-Dawley rats. Explants are taken at 14 and 28 days and evaluated histologically for compatibility, cartilage growth, and maintenance of the differentiated phenotype based on staining for aggrecan and type II collagen.

For the in vivo tests, a carrier of the present invention containing an osteogenic agent may be evaluated for the capabilities for supporting osseous healing in a rat cranial defect model by implantation into a 5 mm by 3 mm defect created in the parietal bone of 6 weeks old male Sprague-Dawley rats. The defects are evaluated at 28 days by radiographic and histologic analysis.

The in vivo model for cartilage repair is a full-thickness articular cartilage defect in the rabbit (Amiel et al., 1985, *J. Bone Joint Surg.* 67A:911). Defects measuring approximately 3.7 mm in diameter and 5 mm deep defect are created in the center of the medial femoral condyles of adult male New Zealand white rabbits. The defects are then either filled with carrier containing a chondrogenic agent or left unfilled as controls. The defects are evaluated morphologically and histologically at 6 and 12 weeks and then at 6 months and one year.

The following examples are provided for purposes of illustration and are not intended to limit the invention in any way.

EXAMPLE I

Preparation of Hyaluronate-amine Derivative

Free amine groups were introduced to hyaluronate (HA) (Lifecore Biomedical having a molecular weight of $1.3 \times 10^6$) by the reaction of hyaluronate with ethylenediamine in the presence of water soluble carbodiimide, 1-(3-dimethylaminopropyl)-3-ethycarbodiimimide hydrochloride (EDC). Diamine compounds and EDC (Aldrich) in extreme excess are required.

HA 0.4 grams (about 1 mmole of repeat units) in 100 ml PBS (10 mM, pH 7) and 6.7 mls of ethylenediamine (100 mmole) were combined followed by adjusting the solution to pH 5.0 using HCI. 4.02 grams of EDC (210 mmole) was added to the solution and the reaction was allowed to proceed at room temperature for 24 hours and then dialyzed against 4 liters of deionized water 4 times for a total of 24 hours, thereby removing any unreacted ethylenediamine or EDC prior to the cross-linking reaction so that the cross-linking reaction proceeds without utilizing extraneous cross-linking or ionic binding agents.

Under this condition, about 20% of carboxyl groups in the sugar chain were converted to amine groups.

EXAMPLE II

Preparation of Polysaccharide-polyaldehyde Derivatives

HA/polyaldehyde (HA-pAld)was prepared by the oxidation of hyaluronate using sodium periodate as an oxidizer. HA 1 gram was dissolved in 80 ml deionized water to which was added 20 ml of 0.5 M sodium periodate. After reaction at room temperature in the absence of light for 18 hours, glycerol was added to quence the unreacted periodate, and dialized against a large volume of deionized water. The dialized HA-pAld solution was lyophilized and the resulting white powder was stored in the dark at 4° C. Under this condition, about 5% of the repeat units in HA were oxidized. The concentration of active aldehyde in the macromolecular chain is controlled by changing the oxidation conditions, for example, the reaction time and amount of oxidizer.

Active aldehyde groups carrying chondroitin sulfate (Sigma)(CS-pAld) were prepared by the same method as above.

EXAMPLE III

Preparation of HA-NH2/HA-pAld Gel 0.2 grams of HA-NH2 and 0.4 grams of HA-pAld were dissolved in 50 ml of deionized water separately. Each of the solutions contained 100 micromole of active groups. The two solutions were mixed at room temperature under vigorous stirring. A gel formed after 20 minutes. The gel thus formed was stable in water at a pH range of 0.1 M HCl to 0.1 M NaOH.

EXAMPLE IV

Preparation of HA-NH2/HA-pAld Sponge

The HA-NH2/HA-pAld gel prepared as in Example III was frozen at −78° C. and then dried under vacuum at −4° C. for 4 hours, −2° C. for 8 hours, −4° C. for 20 hours, and 18° C. for 1 hour.

EXAMPLE V

Preparation of HA-NH2/CS-pAld

The HA-NH2/CS-pAld gel and sponge were prepared by the methods disclosed in Example III and IV above except for the substitution of CS-pAld for HA-pAld.

EXAMPLE VI

Preparation of HA-NH2/HA-pAld Carrier having Crystal Violet Encapsulated 2.0 mls of crystal violet solution (1% Sigma) was added to 23 mls of deionized water containing 0.2 g HA-NH$_2$ (free amine content, 100 micromole). The solution was mixed with 25 mls of HA-pAld solution (aldehyde content, 100 micromole) at room temperature under vigorous stirring. A gel formed after 20 minutes. The gel thus formed was incubated with 500 ml of deionized water at room temperature, and the water was sampled and replaced at the time points 1, 2, 4, 6, 8 and 18 hours. The crystal violet released from the gel was monitored by measuring the O.D. of sampled solutions at 590 nm. The release curve is shown in FIG. 1.

EXAMPLE VII

Preparation of HA-NH2/HA-pAld Carrier having a Therapeutic Agent Immobilized.

Albumin, bovine-fluorescein isothiocyanate (FITC-BSA, Sigma) was chosen as a model for therapeutic proteins. 10 mgs of FITC-BSA in 2 mls of deionized water was added to 23 mls of Ha-pAld solution (HA-pAld content, 4 g; aldehyde content, 100 micromole). The solution incubated at room temperature for 20 minutes, then mixed with 25 mls of HA-NH$_2$ solution (HA-NH$_2$ content, 0.2 g; free amine content, 100 micromole) followed by incubation at room temperature for an additional 20 minutes. The gel thus formed was incubated in 500 ml of deionized water at room temperature. The incubation medium was replaced at time points 1, 2, 4, 6, 8, 24, 48 hours and every two days thereafter for two weeks. The release of FITC-BSA in the incubation medium was determined by measuring the O.D. at 495 nm. As shown in FIG. 2, about 12% of the FITC-BSA released from the carrier in the first two hours; after that time no significant amount of protein could be found, indicating that the remaining protein was covalently immobilized in the gel.

EXAMPLE VIII

Incorporation of Growth Factor into Matrices

Basic fibroblast growth factor (bFGF) was incorporated into HA gels either by addition to HA(I) (prepared as in Example I) solution following mixing with HA(II) (prepared as in Example II) or by incubation of bFGF with HA(II) solution at 4° C. overnight prior to mixing with HA(I). These two formulations were recorded as HA(I/II) and HA(II/I), respectively. Incubation with HA(II) covalently links the growth factor to the HA via imine bonds. The final concentration is: 1 mg of bFGF, 2 mg of HA(I), and 2 mg of HA(II) in 1 ml of sucrose buffer without EDTA. Radioactive $^{125}$I-bFGF was used as a tracer for the samples prepared for release kinetics study. Viscous hyaluronate solution (4%, W/V) containing bFGF (1 mg/ml) was used as control.

For an in vivo rat cranial defect assay, growth factor incorporated HA sponge was prepared by diffusion of bone morphogenetic protein (BMP) into pre-dried HA sponge (5×4×3 mm.L.W.H.) at the rate of 30 μg per piece of the sponge followed by lyophilization.

EXAMPLE IX

Study of Release of Growth Factor In Vitro

A six well format cell culture insert equipped with PET membrane with the pore size of 0.4 μm was used for the in vitro bFGF release study. Sodium citrate buffer (20 mM, pH 5) containing sucrose (9%) and EDTA (1 mM), and DMEM cell culture medium were chosen as release media. Then 40 mg of each sample (HA (I/II), HA (II/I), HA sponge and control, as described in Example VIII) with 2.0 ml of medium were placed in the wells, another 4.0 ml of medium were added to the outside chamber. The plates were mounted on an orbital shaker platform and shaked at 37° C. constantly. The release medium in the outside chamber was counted for radioactivity by a liquid scitillation counter (Beckman, LS 6500) at desired time points and refreshed. About 68, and 90% of incorporated bFGF were released from HA viscous solution into the DMEM cell culture medium in 4 hrs., and 8 hrs., respectively. The remaining bFGF was released in one more day. After incubation for 4 hrs., 8 hrs., and 24 hrs., about 62, 78, and 88% of the encapsulated bFGF in HA (I/II) was released, respectively. The remaining bFGF was released completely in another two days. The type of release medium seems to have no effect on the bFGF release rate. For HA (II/I) gel, only 16, 25, and 30% of incorporated bFGF was released from the gel to sucrose buffer after incubation for 4 hrs., 1 day and 2 days, respectively. The remaining bFGF was released for 2 more weeks. When DMEM cell culture medium was chosen as the release medium, only 13, 15, and 17% of bFGF released from HA (II/I) for the same time period, and 20% of bFGF still remained in the gels after 2 weeks incubation when the experiment was terminated.

EXAMPLE X

Subperiosteal Injection in Rat Calvaria

Six week old male Sprague Dawley rats received 50 μl injections under the periosteum of the left parietal bone of samples described below. After 14 days, calvaria were harvested and processed for histological evaluation. The parietal bone thicknesses are given below.

|  | Parietal bone thickness, μm (mean ±SD, n = 6) |
|---|---|
| No treatment | 259 ± 30 |
| HA gel | 276 ± 94 |
| HA (I/II) + 1mg/ml bFGF | 451 ± 97 |
| HA (II/I) + 1mg/ml bFGF | 523 ± 81 |
| 1 mg/ml bFGF in buffer | 350 ± 35 |
| 1 mg/ml bFGF in solution HA | 281 ± 30 |

What is claimed is:

1. An injectable biodegradable carrier for the delivery of therapeutic agents, said carrier comprising
   a first polysaccharide cross-linked to a second polysaccharide, wherein said first and second polysaccharides is each a member selected from the group consisting of hyaluronic acid, dextran, dextran sulfate, chondroitin sulfate, dermatan sulfate, keratan sulfate, heparin, heparan sulfate and alginate;
   and wherein said first and second polysaccharides are covalently cross-linked to each other through imine bonds between amino groups on said second polysaccharide and aldehyde groups from oxidized sugar rings on said first polysaccharide.

2. The carrier of claim 1 wherein said first polysaccharide is the same as said second polysaccharide.

3. The carrier of claim 2 wherein said first and said second polysaccharide are both hyaluronate.

4. The carrier of claim 1 wherein said first polysaccharide is different from said second polysaccharide.

5. The carrier of claim 4 wherein said first polysaccharide is hyaluronate and said second polysaccharide is chondroitin sulfate.

6. A carrier according to claim 1 wherein said first polysaccharide contains an excess of aldehyde groups such that free aldehyde groups remain subsequent to cross-linking to said second polysaccharide.

7. A therapeutic composition comprising an injectable biodegradable carrier and a therapeutic agent, said carrier comprising a first polysaccharide cross-linked to a second polysaccharide, wherein said first and second polysaccharides is each a member selected from the group consisting of hyaluronic acid, dextran, dextran sulfate, chondroitin sulfate, dermatan sulfate, keratan sulfate, heparin, heparan sulfate and alginate; and wherein said first and second polysaccharides are covalently cross-linked to each other through imine bonds between amino groups on said second polysaccharide and aldehyde groups from oxidized sugar rings on said first polysaccharide.

8. The composition of claim 7 wherein said therapeutic agent is selected from the group consisting of growth factors, cytokines, hormones and DNA constructs.

9. The composition of claim 8 wherein said therapeutic agent is an osteogenic agent.

10. The carrier of claim 1 in a gel-like form.

11. A method for preparing an injectable biodegradable carrier for delivery of therapeutic agents in a gel-like form, said method comprising a step of reacting a first polysaccharide derivative having aldehyde groups with a second polysaccharide under conditions whereby said aldehyde groups covalently react to cross link with said second polysaccharide to form said carrier and wherein said first and said second polysaccharides are independently selected from the group consisting of hyaluronic acid, dextan, dextran sulfate, chondroitin sulfate, dermatan sulfate, keratan sulfate, heparin, heparan sulfate and alginate.

12. The method according to claim 11 wherein said method further comprises a step of oxidizing said first polysaccharide to form said first polysaccharide derivative.

13. The method of claim 11 wherein said first polysaccharide is the same as said second polysaccharide.

14. The method of claim 13 wherein said first and said second polysaccharide are both hyaluronate.

15. The method of claim 11 wherein said first polysaccharide is different from said second polysaccharide.

16. The method of claim 15 wherein said first polysaccharide is hyaluronate and said second polysaccharide is chondroitin sulfate.

17. The method of claim 12 wherein said step of oxidizing said first polysaccharide comprises treatment of said first polysaccharide with periodate.

18. The method according to claim 11 wherein said first polysaccharide derivative contains an excess of aldehyde groups such that free aldehyde groups remain subsequent to cross-linking to said second polysaccharide.

19. A method of delivering a therapeutic agent in vivo, comprising a step of administering a composition of claim 7 at a site of desired delivery.

20. A method of inducing bone growth in vivo comprising a step of administering a composition of claim 9 at a site of desired bone growth.

21. The composition of claim 8 wherein said therapeutic agent is covalently bonded to said carrier.

22. The composition of claim 8 wherein said therapeutic agent is entrapped within said carrier.

23. The composition of claim 21 or 22 wherein said agent comprises an osteogenic agent.

24. The composition of claim 23 wherein said agent comprises bFGF.

25. The method of claim 11 further comprising the step of reacting said first polysaccharide derivative with a therapeutic agent prior to reaction with said second polysaccharide.

26. The method of claim 25 wherein said therapeutic agent is selected from the group consisting of growth factors, cytokines, hormones and DNA constructs.

27. The method of claim 26 wherein said agent comprises a growth factor.

28. The method of claim 27 wherein said growth factor comprises bFGF.

29. A method of delivering a therapeutic agent in vivo, comprising a step of administering a composition of claim 21 or 22 at a site of desired delivery.

30. A method according to claim 29 wherein said agent comprises bFGF.

* * * * *